(12) United States Patent
Wilde (10) Patent No.: US 12,318,310 B2
(45) Date of Patent: Jun. 3, 2025

(54) JOINT IMPLANT EXTRACTION AND PLACEMENT SYSTEM AND LOCALIZATION DEVICE USED THEREWITH

(71) Applicant: Jeffrey Wilde, San Diego, CA (US)

(72) Inventor: Jeffrey Wilde, San Diego, CA (US)

( * ) Notice: Subject to any disclaimer, the term of this patent is extended or adjusted under 35 U.S.C. 154(b) by 0 days.

(21) Appl. No.: 18/444,571

(22) Filed: Feb. 16, 2024

(65) Prior Publication Data

US 2024/0189113 A1 Jun. 13, 2024

Related U.S. Application Data

(63) Continuation of application No. 17/321,491, filed on May 16, 2021, now Pat. No. 11,931,267.

(60) Provisional application No. 63/025,792, filed on May 15, 2020.

(51) Int. Cl.
  *A61F 2/46* (2006.01)
  *A61B 17/92* (2006.01)
  *A61B 34/10* (2016.01)
  *A61B 34/20* (2016.01)
  *A61B 34/30* (2016.01)

(52) U.S. Cl.
  CPC ............ *A61F 2/4603* (2013.01); *A61B 17/92* (2013.01); *A61B 34/10* (2016.02); *A61B 34/20* (2016.02); *A61B 34/30* (2016.02); *A61B 2034/102* (2016.02); *A61B 2034/2048* (2016.02); *A61F 2002/4619* (2013.01)

(58) Field of Classification Search
  CPC ................ A61B 17/1604; A61B 17/92; A61B 2017/1602; A61B 2034/102; A61B 2034/108; A61B 2034/2048; A61B 2034/2055; A61B 2034/2065; A61B 2090/3983; A61B 34/10; A61B 34/20; A61B 34/30; A61B 34/32; A61F 2/30; A61F 2/32; A61F 2/38; A61F 2/4603; A61F 2002/4619; A61F 2002/4632
  See application file for complete search history.

(56) References Cited

U.S. PATENT DOCUMENTS

2018/0014891 A1\* 1/2018 Krebs ................... A61B 5/055

\* cited by examiner

*Primary Examiner* — Samuel S Hanna
(74) *Attorney, Agent, or Firm* — Timothy Marc Shropshire (57) ABSTRACT

An implant localization device includes a coupler and a positioning system. The coupler is configured to removably engage an implant component to fix the positioning system in space relative to the implant component. The positioning system is in communication with a centralized computing system, whereby, due to the fixed spatial relationship between the positioning system and the implant component, via the coupler, and determinable changes in movement relative to a registered starting point, the centralized computing system is able to calculate a real-time position and orientation of the implant component. The centralized computing system is configured to synthesize data from a joint templating software program, a CAD software program, and the positioning system to provide real-time positional and orientation data to assist with extraction and placement of the implant component. Robotics and reference markers may be used to further automate and/or enhance the accuracy and efficiency of the system.

11 Claims, 7 Drawing Sheets

JOINT IMPLANT EXTRACTION AND PLACEMENT SYSTEM AND LOCALIZATION DEVICE USED THEREWITH

CROSS-REFERENCE TO RELATED APPLICATION(S)

This application is a continuation of U.S. Nonprovisional patent application Ser. No. 17/321,491 filed May 16, 2021, (now U.S. Pat. No. 11,931,267, issued Mar. 19, 2024), which claims the benefit of U.S. Provisional Patent Application No. 63/025,792 filed May 15, 2020, the entire disclosures of which are incorporated by reference herein.

BACKGROUND OF THE INVENTION

1. Field of Invention

The present invention relates to systems and apparatuses for automating the extraction and placement of joint implants in joint replacement procedures.

2. Description of Related Art

Implant Extraction

Joint revision surgery, whether for a hip, a knee, a shoulder, an ankle, an elbow, or any other joint that is a candidate for revision surgery, is a procedure in which the surgeon removes a previously implanted artificial joint, i.e., a prosthesis, and replaces it with a new prosthesis. The first stage in joint revision surgery is the removal of the old prosthesis. Extraction of the joint components is often the most difficult aspect of the revision procedure and ultimately dictates what is required for the final reconstruction.

Revision surgery typically involves the use of a cutting tool, such as a high-speed burr-tip rotary tool, a ballistic chisel powered by controlled bursts of pressurized nitrogen, manual osteotomes or flexible Steinmann pins drilled around the prosthesis. These tools are used to break up pieces of cement or bone from an implanted prosthesis, but can also be used to loosen a prosthesis that was held in place by a press fit. The surgeon generally uses these tools blindly, i.e., without real-time feedback of the location of the tool relative to the prosthesis, in an attempt to disrupt the interface between the bone/cement and the prosthesis. If the surgeon is unable to adequately disrupt the interface between the bone/cement and the prosthesis using the cutting tools, then an osteotomy may need to be performed to facilitate prosthesis removal. For example, hip revision surgery may require an extended trochanteric osteotomy (ETO), whereby the femur is cut in half, using a hand saw or burr to facilitate removal of the implant, which results in significant morbidity to the patient and increased operating time.

Some prosthetic components, such as a hip cup, oftentimes require the use of a slap hammer, or similar device, coupled to a threaded hole in/on the prosthetic component and/or a manual cutting tool for extraction. One such device is disclosed in U.S. Pat. No. 7,998,146B2 to Anderson. U.S. Pat. No. 7,998,146B2 discloses a hip cup extraction apparatus comprising a shaft, a handle, a semicircular cutting blade, a spring-loaded latching member, and a head for removing a hip cup from a pelvic bone. The head is inserted into the hip cup. Force may then be applied to the hip cup extraction apparatus in order to drive the semicircular cutting blade into the pelvic bone. The hip cup extraction apparatus may then be rotated or pivoted such that the semicircular cutting blade passes completely around the hip cup.

Currently, all technologies for extraction of prostheses, particularly with regard to cutting, are performed manually. As with any procedure performed by a human, there are a number of issues that can arise with manual extraction. These issues include, but are not limited to: (i) time-consuming procedures that increase the patient's susceptibility to surgical complications; (ii) bone loss due to the surgeon's inability to navigate with absolute accuracy and precision, resulting from the surgeon's inability to determine the precise location/contour of the implant; and (iii) bone fracture from stresses on the bone(s), e.g., from the use of a slap hammer and/or a manual chisel/blade, etc.

Implant Placement

When placing an implant, either in a primary joint replacement procedure or a joint revision procedure, care must be taken to properly seat the implant to, among other things, restore normal joint mechanics. For example, one of the goals of femoral stem placement in hip replacement procedures includes restoration of normal hip mechanics, which requires consideration of (i) medial offset, (ii) leg length, i.e., vertical height, (iii) femoral anteversion, and (iv) center of rotation. Vertical height is determined by where the center of the femoral head sits, i.e., the center of rotation. Vertical height can be affected if the stem is not accurately positioned, e.g., if it is set too deep or, conversely, not deep enough into the femur. Vertical height can be adjusted by the stem vertical position in the femur as well as using modular femoral heads with different diameters and neck lengths. However, adjusting the vertical height by using femoral heads will likewise affect the medial/lateral offset, which may result in complications including discomfort to the patient or possible instability of the total hip arthroplasty resulting in dislocation. Thus, proper placement of the stem is critical for stem fixation as well as ensuring that the proper femoral head is used, thereby mitigating incidence of malalignment/complications.

To prevent component malposition and a postoperative leg length discrepancy, surgeons typically combine x-rays of the patient's hip with overlay schematics of the hip replacement prosthesis. This process is known as templating and allows the surgeon to make an initial determination of the size of the implants needed at the time of surgery, the size of the leg length discrepancy needing correction, and how much bone that will need to be removed intraoperatively. However, it is difficult to achieve accurate positioning of implants and assess the numerical value of implant positioning in primary hip replacement procedures using conventional methods. In an attempt to address these deficiencies, surgeons are now using computer-guided systems and robotics to help confirm the position and size of the hip replacement implants during surgery. The computer-guided templating and navigation systems show the patient's bony anatomy on-screen to help guide the surgeon in positioning the implants. In cases in which robotics are utilized, the navigation system guides the robotic arm/surgeon, in an automated or semi-automated fashion, with implant placement.

Additionally, sensor arrays are used in primary implant procedures to localize the bone for the navigation system to ensure the positioning of the implant matches the templated parameters desired by the surgeon in real-time.

Fluoroscopy is often used in conjunction with, or as an alternative to, computer-guided/navigation systems to help guide surgeons during implant placement. To ensure proper depth of the implant, intermittent fluoroscopy scans, e.g., x-rays, must be performed intraoperatively to analyze current placement of the implant and determine what adjustments may be necessary to properly seat the implant. The intermittent scans are not performed in a way that they can be viewed in real-time while performing the procedure without placing the surgical staff at risk for excessive x-ray/fluoroscopic exposure. Fluoroscopy is also limited by the 2-D spatial orientation, parallax (which can alter the accuracy of the images), patient mal-positioning (which can make high quality images more difficult to obtain in the intra-operative theater), and difficulties identifying good bony landmarks on both femurs and the pelvis. Thus, the surgeon is unable to ensure precise and accurate seating of the implant in real-time.

The foregoing discussion demonstrates the current barriers in implant placement accuracy in total hip replacement. However, it should be noted that any total joint replacement surgery, whether for a knee, a shoulder, an ankle, an elbow, or any other joint is subject to the same challenges with recreating the joint mechanics and implant placement.

Based on the foregoing, there is a need in the art for automated systems for extracting and placing joint implants in primary and revision procedures that provide real-time positioning data, thereby allowing such procedures to be performed in a more efficient manner with increased precision and accuracy, decreasing radiation exposure, while mitigating bone loss and, hence, undue stress to the patient and the likelihood of surgical complications.

SUMMARY OF THE INVENTION

According to an embodiment of the present invention, the system for extracting and placing joint implants includes a centralized computing system, a joint templating software program configured to compare joint scans with overlay schematics of an implant component, a CAD software program configured to analyze a computer-generated design of the implant component, and a localization device for localizing an implant component in space. The localization device includes a coupler and a positioning system, wherein the coupler is configured to removably engage the implant component (e.g., via engagement with the trunnion on a femoral stem, a threaded insertion hole on an acetabular shell, insertion points on femoral/tibial components in total knee arthroplasty, etc.) to fix the positioning system in space, in a known position and orientation, relative to the implant component. The positioning system comprises one or more sensors, e.g., line-of-sight sensors, which are registered with the centralized computing system pre-operatively or intra-operatively, whereby the centralized computing system is able to use data from the positioning system to determine changes in position and orientation of the positioning system, relative to its starting position and orientation, thereby allowing the computing system to calculate a real-time position and orientation of the positioning system, whereby, due to the fixed spatial relationship between the positioning system and the implant component, via the coupler, the centralized computing system is able to calculate a real-time position and orientation of the implant component. The centralized computing system is configured to synthesize data from the joint templating software program, the CAD software program, and the positioning system to provide real-time position and orientation data regarding the implant component to assist with extraction and placement of the implant component.

In an embodiment, the system includes a robotic arm in communication with the centralized computing system. The robotic arm is registered with the centralized computing system pre-operatively or intra-operatively. Once registered, the centralized computing system is able to determine the real-time position and orientation of the robotic arm. Means for tracking the position and orientation of robotics are known to those skilled in the art and can be carried out in a number of ways. Any such means can be used with the present invention without deviating from the scope of the invention. The robotic arm is configured to execute instructions received from the centralized computing system, wherein the instructions are based on information including, but not limited to, the synthesized data, i.e., the combined data from the joint templating software program, the CAD software program, and the positioning system.

In an embodiment, the robotic arm includes a cutting tool configured to facilitate extraction of the implant component.

In an embodiment, the system includes one or more reference markers. The reference marker(s) is/are registered with the centralized computing system, whereby the centralized computing system is able to monitor the real-time position and orientation of the references marker(s). In such an embodiment, the instructions transmitted to the robotic arm from the centralized computing system also include the real-time position and orientation of the reference marker(s). In such an embodiment, reference marker(s) are analyzed by the centralized computing system to track the real-time orientation and position of the bones and other anatomic structures relative to the other components in the system (e.g. robotic arm, coupler/implant, etc.)

In an embodiment, the robotic arm comprises an insertion tool configured to facilitate placement of the implant component.

In an embodiment, the system includes a probe configured to register virtual points, which may include reference marker(s) (reference markers would need to be registered with a probe in applications where the reference markers do not have a tracking device, e.g. line-of-sight array, integrated into the reference markers for tracking by centralized computing system), points on bone, points on implants, etc., with the centralized computing system. Once registered, the centralized computing system is able to determine the real-time position and orientation of the registered virtual points.

In an embodiment, the centralized computing system is configured to analyze the real-time position of the coupler relative to the real-time position of the reference marker(s) (and/or virtual reference points), i.e. triangulation, to determine the real-time joint parameters of the implant component. (e.g., hip vertical position, leg length, medial offset, center of rotation etc. in hip applications; joint line, implant rotation, varus/valgus alignment, etc. in knee applications, etc.)

In various embodiments, the coupler may be any suitable configuration that allows it to releasably couple to the implant component to fix the positioning system in space relative to the implant component. A non-exhaustive list of example configurations for the coupler include a sleeve, a clamp, or a rod.

In an embodiment, the positioning system is integrally formed as part of the coupler, whereby the positioning system and the coupler are a single, unitary component. Alternatively, in an embodiment, the positioning system is removably coupled to the coupler. When coupled, the positioning system and the coupler are configured to maintain a fixed position and orientation relative to one another until decoupled.

In an embodiment, the positioning system includes an inertial sensor. In various embodiments, the inertial sensor is an accelerometer, a gyroscope, or a combination accelerometer/gyroscope.

In an embodiment, the positioning system includes a sensor array (i.e. visual array).

In an embodiment, the system includes a database of implant component designs, wherein the CAD software program is configured to analyze an implant component design selected by a user from the database and render accurate implant dimension data for use by the centralized computing system.

In an embodiment, if dimension data is not available for the implant, the CAD software program is also able to synthesize data from virtually registered points, using a probe, on implant components to extrapolate the contours of the implant for dimension data of the implant component for use by the centralized computing system.

The present system monitors movement of the implant component by monitoring changes in the position and orientation of the implant component—determined by the centralized computing system, based on changes in the position and orientation of the localization device as tracked by the centralized computing system. Based on changes in the position and orientation of the localization device, relative to the initial position and orientation of the localization device (established when registering the localization device with the centralized computing system), and the fixed spatial relationship between the localization device and the implant component, the system can determine the real-time position and orientation of the implant component in 3-dimensional space.

Similarly, based on changes in the position and orientation of the system components (robotic arm, reference markers/reference points, etc.), relative to their respective baseline, i.e., starting, positions and orientations determined at the time of registration of the system components with the centralized computing system, the system can determine the real-time position and orientation of each of the system components, e.g., the cutting tool of the robotic arm, in 3-dimensional space. By comparing the real-time position and orientation of the implant with the real-time position and orientation of the system components (via positioning/mapping software, for example), the system can determine the real-time spatial relationship between/among the system components, anatomic structures, and the implant component, i.e. triangulation.

The system's ability to synthesize the position and orientation data of the implant component and the system components with the dimensional/contour data of the implant component (provided by the CAD software) and the placement/sizing/fitment data (provided by the templating software) optimizes the overall accuracy and precision of the present system when extracting and placing implant components as well as recreating or restoring desired joint parameters.

This system can be used to facilitate (i) implant extraction in revision procedures, (ii) implant placement following implant extraction in revision procedures, and (iii) implant placement in primary joint replacement procedures, each of which are summarized below.

Joint Replacement Implant Extraction Application

In an embodiment, the present system is used to extract implant components in revision procedures. Due to the fixed spatial relationship between the positioning system and the implant component, via the coupler, the centralized computing system is able to monitor, in real-time, the movement and, hence, the spatial orientation and position of the implant component—based on data received by the centralized computing system from the positioning system. The computerized joint software/templating system combines imaging (e.g., x-rays, CT scan, etc.) of the patient's bony anatomy with overlay schematics of the replacement prosthesis to aid in the joint reconstruction. The centralized computing system synthesizes the computerized joint software/templating system data, the CAD implant data, the positioning system data (regarding the real-time position and orientation of the implant component in space), and reference markers/points data, to ensure absolute accuracy and precision of the dimensional aspects/contour of the implant component, the implant component position and orientation in space, and the patient's bony anatomy to aid in the extraction and reconstruction process.

In an embodiment, the CAD software program is configured to analyze an implant component design selected by a user from the database of implants, allowing the centralized computing system to provide accurate implant dimensional data and instructions to the robotic arm. If an implant is not found in the database, the visible surface of the implant (i.e., the contours and dimensions) can be determined real-time using a probe, with a positioning sensor, e.g., a line-of-sight or other wireless sensor in communication with the centralized computing system, affixed to it, whereby the user "paints" the surface of the implant to provide reference points for the CAD program to extrapolate the contour and dimensional data for the implant.

In various embodiments, one or more reference points (e.g., the shoulder of the femoral implant, identification of ingrowth/ongrowth surfaces, a threaded insertion hole on the shoulder, etc.), in addition to the coupler, are registered on the implant to increase the accuracy of the implant position and orientation in space. The reference points may be virtually placed on the implant using a probe in communication (wired or wireless) with the centralized computing system. Alternatively, the reference points may be physically attached to the implant, whereby the reference points are in communication (wired or wireless) with the centralized computing system. The centralized computing system then guides the robotic arm (which may be automated or semi-automated) to cut the implant from the bone/cement interface with absolute accuracy and precision based on the precise measurements and real-time position and orientation of the implant, as determined by data provided by the CAD software program, the joint software/templating system, and the positioning system.

The system's ability to determine the real-time spatial relationship between/among the system components, e.g., the robotic arm, etc., and the implant component allows the centralized computing system to instruct the robotic arm in real-time in response to changing conditions. For example, if the position and/or orientation of the implant is altered during the extraction procedure, the robotic arm will make the necessary adjustments in real-time, in accordance with the instructions from the centralized computing system, to ensure absolute accuracy and precision in extracting the implant. Since the dimensions of the implant and its position and orientation is "known" and tracked by the centralized computing system, the robotic arm cutting tool can make the cut directly adjacent to the implant or a predetermined distance from the bone/implant interface (e.g. make the cut with 1 mm bone remaining on the implant, etc.)

The fixed spatial relationship between the positioning system and implant component, combined with real-time position and orientation data of the positioning system, as determined by the centralized computing system (which allows real-time position and orientation of the implant component to be determined), eliminates the need to insert bone pins or affix reference points to the bone to localize the implant for extraction (bone pins/reference markers are only required for implantation of components). The fixed spatial relationship between the positioning system and implant component, combined with real-time position and orientation data of the positioning system, as determined by the centralized computing system (which allows real-time position and orientation of the implant component to be determined), can also be utilized with the same degree of accuracy in applications where an osteotomy is required to aid in the extraction of the implant, e.g., an extended trochanteric osteotomy (ETO), etc.

Joint Replacement Implant Placement—Following Extraction

In an embodiment, the position data of the original/ extracted implant can be useful for reconstruction of the joint following implant extraction, e.g., with placement of the revision components to recreate or correct the original joint mechanics. In such an embodiment, bone reference markers (e.g., a unicortical screw, a cortical button, a superficial registration point, visual array, small drill hole in bone, etc.) are placed in the bones prior to affixing the localization device (i.e., the coupler and positioning system) to the implant. The reference markers are used to reference the position of the original implant (before extraction) in relation to the bones (e.g., femur and acetabulum/pelvis in hip applications, femur and tibia in knee applications, etc.). The reference markers can then be registered with the centralized computing system so that the original joint parameters (e.g., hip vertical position, leg length, medial offset, center of rotation etc. in hip applications; joint line, implant rotation, varus/valgus alignment, etc. in knee applications, etc.) can be determined/calculated. Once the bone reference markers are registered and data is collected on the original implants (based on the spatial position of the implants relative to the bone reference markers), implant extraction can occur, as described above.

Additionally, bony registration and mechanical axis registration may be required after implant extraction to compare against the bony reference markers placed prior to implant extraction. The bone reference markers remain in the bone and can then be used as reference points to reconstruct the joint parameters with the coupler attached to the revision implants. This aids in placement of the revision implant components with real-time feedback on important joint replacement parameters in comparison to the original implants (e.g., vertical height, leg length, offset, anteversion, etc. in hip applications; joint line, implant rotation, varus/valgus alignment, etc. in knee applications). This real-time feedback on important joint replacement parameters allows the surgeon to adjust the modular features of the implants needed to correct the joint parameters prior to trialing the construct. For example, in hip revision surgery the revision femoral component can be placed in the bone and the localization device can then be attached to the component trunnion (trial or final) to register the center of rotation (which would also account for offset, leg length) against the reference markers. If, for example, the system found the revision components' new center of rotation position to result in a construct that is 3 mm short in leg length and offset from the original extracted implant's center of rotation position, the surgeon would immediately know the specific modular head needed to move the new center of rotation to recreate the original hip mechanics, this would also allow the surgeon to know the changes that would alter the original joint mechanics if desired. This could all be done prior to reducing the hip and trialing the construct. In current practice, the surgeon would need to reduce the hip and trial multiple different head options to determine this information, increasing surgical time and tissue trauma with repeated reductions and dislocations. Additionally, an x-ray or fluoroscopic image is often taken to help determine the correct leg length, offset, etc. which increases the radiation risk to all personal involved. As another example, in a knee application, this system would allow the surgeon to know the original joint line position (e.g., distal femoral implant position, gap balance, etc.) as referenced by the data from the extracted implant. Following extraction, the surgeon can reference the remaining distal femoral bone cuts (e.g., with a probe, etc.) against the bone reference markers and adjust distal augments or polyethylene insert size to recreate the joint line in real-time prior to trialing the construct. This would increase both efficiency of the reconstruction procedure as well as accuracy.

This system can be used with or without robotic assistance. In robotic applications, the robotic arm could be used to cut/prepare/broach the bone to the correct contour to match the revision components and based on the data collected prior to implant removal. Modular selection of implants to build the revision components would proceed as described above and the robotic arm would assist with implantation of the implants. In some embodiments, the robotic arm may not aid in implant placement. In non-robotic applications, following implant extraction, the bone would be prepared by traditional methods, e.g., using cutting blocks/jigs/broaches, manual cutting, etc., to prepare the bone for revision components, but the modular selection of implants would proceed as described above.

Although specific examples are discussed herein, one skilled in the art would understand and appreciate that this application is not limited to these specific examples and is applicable to the other modular aspects of revision and primary joint replacement components (e.g., modular bodies of femoral components, different acetabular liners, different femoral neck angles/offsets, etc. in the hip model; knee joint line, distal/posterior femoral condyle augments, component rotation, tibial component position/slope, polyethylene liner thickness, etc. in the knee model; etc.).

Primary Hip Replacement Femoral Component Insertion Application

In an embodiment, the present system can be used for placing joint implants in primary applications, which can be done with or without robotic assistance.

Prior to performing the femoral neck cut, bone reference markers (e.g., a cortical button, a superficial registration point, etc.) are placed and a fluoroscopy shot is taken of the hip including the bone reference markers. This image is used to create a real-time template on the computerized joint software/templating program. The reference markers are a predetermined size to allow appropriate scaling for the template. The remainder of the hip replacement procedure proceeds based on the intra-operative template (e.g., acetabular component placement, femoral bone preparation, etc.) until the femoral trial component (e.g., broach with trial neck, trial femoral component, final femoral component, etc.) is inserted and utilized for trialing of the hip replacement. Once the trial component has been placed in the femur the localization device is attached to the femoral trunnion. The positioning system is then referenced against the bone reference markers to determine the real-time hip center position in relation to the real-time template. This allows the surgeon to adjust implant position as well as select the correct modular femoral head to recreate the native center of rotation, leg length, offset, etc. in real-time and prior to trialing. The implant then can be trialed with the correct modular components. This system can again be used to confirm correct placement of the final femoral stem and selection of the final modular head. This system increases speed and efficiency of implant modularity selection. It also recreates the hip parameters with absolute precision and accuracy.

The foregoing discussion regarding implant extraction and placement in hip revision procedures and implant placement in primary hip replacement procedures is provided in a non-limiting manner, i.e., for illustrative purposes only, to demonstrate use of the present system in revision and primary joint replacement procedures. One skilled in the art would understand that the present system can be similarly used in revision and primary joint replacement procedures for any joint that is a candidate for such procedures.

The foregoing, and other features and advantages of the invention, will be apparent from the following, more particular description of the preferred embodiments of the invention, the accompanying drawings, and the claims.

BRIEF DESCRIPTION OF THE DRAWINGS

For a more complete understanding of the present invention, the objects and advantages thereof, reference is now made to the ensuing descriptions taken in connection with the accompanying drawings briefly described as follows.

DETAILED DESCRIPTION OF PREFERRED EMBODIMENTS

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order-dependent.

The description may use perspective-based descriptions such as up/down, back/front, left/right, and top/bottom. Such descriptions are merely used to facilitate the discussion and are not intended to restrict the application of disclosed embodiments.

The terms "coupled" and "connected," along with their derivatives, may be used. It should be understood that these terms are not intended as synonyms for each other. Rather, in particular embodiments, "connected" may be used to indicate that two or more elements are in direct physical contact with each other. "Coupled" may mean that two or more elements are in direct physical contact. However, "coupled" may also mean that two or more elements are not in direct contact with each other, but yet still cooperate or interact with each other.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous.

Preferred embodiments of the present invention and their advantages may be understood by referring to FIGS. 1-7 wherein like reference numerals refer to like elements.

This system can be used to facilitate (i) implant extraction in revision procedures, (ii) implant placement following implant extraction in revision procedures, and (iii) implant placement in primary joint replacement procedures. The following description provides illustrative, non-limiting examples of how the present system can be used in each of these applications.

Joint Replacement Implant Extraction

Figure 1:
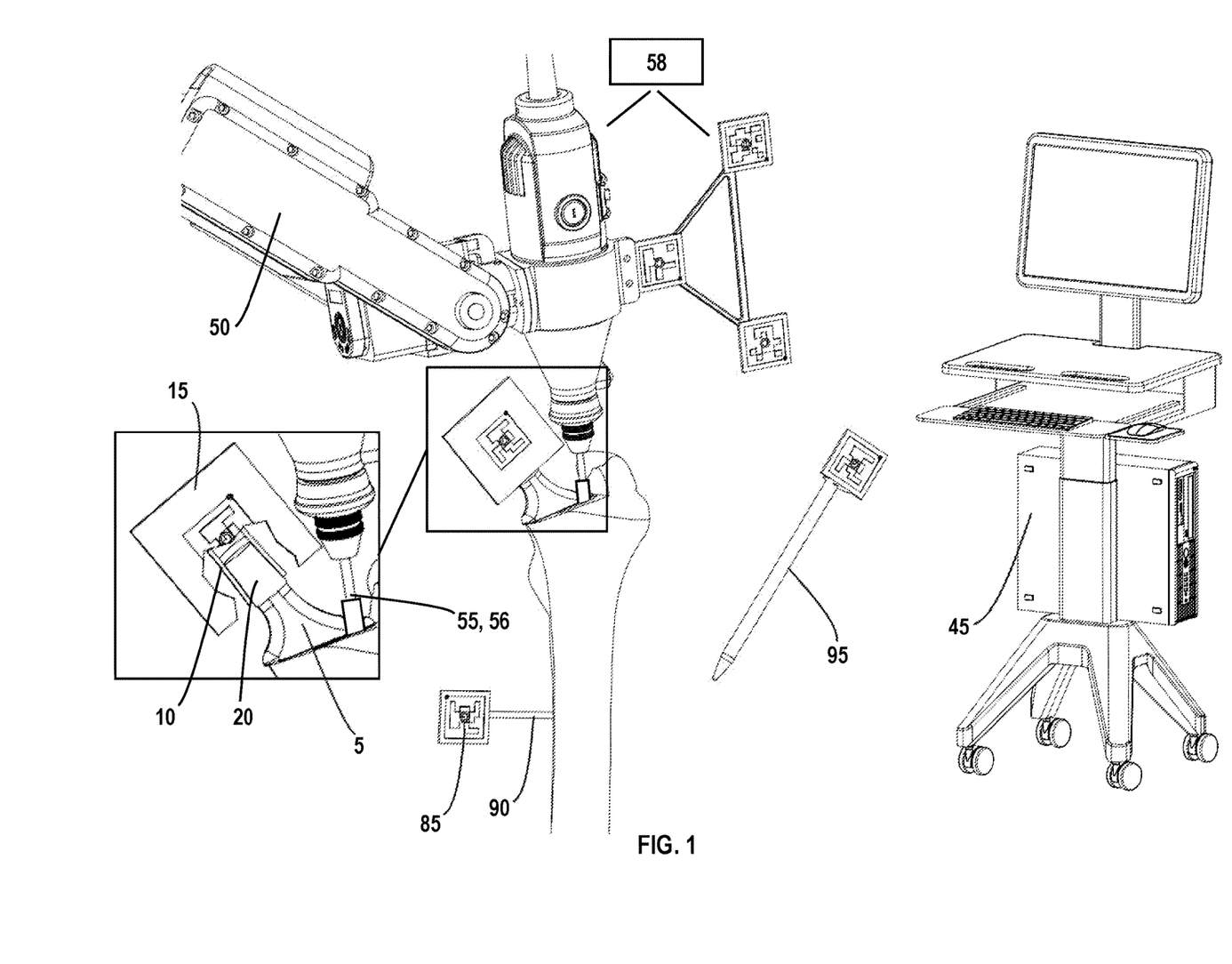
FIG. 1 shows the joint implant extraction and placement system in use with a femoral stem, according to an embodiment of the present invention.

With reference to FIG. 1, coupler 10 is configured to mount to an implant component (i.e., via engagement with the trunnion on a femoral stem) to fix positioning system 15 in a pre-determined position and orientation, relative to the implant component, so that the entirety of the implant component can be localized in space based on this fixed relationship. Based on changes in the position and orientation of positioning system 15, relative to the initial position and orientation of positioning system 15 (established when registering positioning system 15 with centralized computing system 45 preoperatively or intraoperatively), and the fixed spatial relationship between positioning system 15 and the implant component, via coupler 10, centralized computing system 45 is able to determine the real-time position and orientation of the implant component in 3-dimensional space.

In an embodiment, as shown in FIG. 1, coupler 10 is a sleeve that receives trunnion 20, just as the matching female taper of a modular femoral head would. Coupler 10 is configured to engage trunnion 20 using a friction fit, snap fit, or any other suitable releasable engagement mechanism known in the art (e.g., a Morse taper, etc.), whereby, upon engagement, coupler 10, positioning system 15, and femoral stem 5 are fixed, i.e., immobilized, relative to one another. Upon engagement, coupler 10 remains firmly secured in place on trunnion 20 until manually removed.

In an embodiment, positioning system 15 is integrally formed as part of coupler 10, i.e., positioning system 15 and coupler 10 are a single, unitary component. Alternatively, positioning system 15 and coupler 10 are separate components, whereby positioning system 15 is removably coupled to coupler 10. When coupled, positioning system 15 and coupler 10 are configured to maintain a fixed orientation relative to one another until decoupled. Coupler 10 may be coupled to the implant component at the time of manufacturing. Alternatively, coupler 10 may be coupled to the implant component by the surgeon or staff at the time of surgery.

Positioning system 15 includes one or more sensors configured to determine real-time position and orientation of an implant component coupled to positioning system 15. For example, in an embodiment, positioning system 15 includes an accelerometer for measuring the orientation of femoral stem 5 in a stationary state. In a further embodiment, positioning system 15 also includes a gyroscope to supplement the information provided by the accelerometer. Namely, the gyroscope adds an additional dimension to the information supplied by the accelerometer by tracking rotation or twist of a non-stationary femoral stem 5. In an embodiment, as an alternative to the accelerometer and gyroscope, positioning system 15 includes an array of visual/line-of-sight sensors (e.g., infrared arrays, etc.) configured to determine the real-time position of femoral stem 5, relative to the remaining system components, e.g., centralized computing system 45 and robotic arm 50, intraoperatively.

Once coupler 10 engages trunnion 20, positioning system 15 moves in synchrony with femoral stem 5. Thus, if a patient/surgeon were to move the leg during the revision procedure, positioning system 15 would undergo the same movement to the exact degree as femoral stem 5, thereby enabling centralized computing system 45 to determine, based on real-time data from positioning system 15, real-time changes in position and orientation of femoral stem 5. Additionally, one or more reference points (e.g., the shoulder of the implant, insertion threads, ingrowth/ongrowth surface, etc.) on the implant (in addition to coupler 10) may be used in conjunction with the data provided by positioning system 15 to improve accuracy of the system. For example, in an embodiment, virtual reference points are registered with centralized computing system 45 using probe 95 (or other similar device known in the art) without physical attachment to the implant. In such an embodiment, probe 95 (or other similar device) is in communication, wired or wireless, with centralized computing system 45 and is used to interact with the implant to designate reference point(s) that are communicated to centralized computing system 45. Alternatively, reference points (e.g., line-of-sight sensors, etc.) may be physically connected to the implant (e.g., threaded into an insertion hole in femoral stem 5, etc.), whereby the reference points are in wireless communication with centralized computing system 45.

Positioning system 15 is in communication, wired or wireless (e.g., via wireless transmitter, infrared line-of-sight sensor(s), etc.), with centralized computing system 45. Computing system 45 receives and processes data received from positioning system 15. This data is combined with data received from a computer-aided design, i.e., CAD, software program that analyzes computer-generated designs, including dimensional aspects, of the femoral stem 5. Centralized computing system 45 also includes a database of CAD designs with precise dimensional aspects of various femoral stems 5. This allows a user, in preparation for a revision procedure, to select an implant, e.g., by manufacturer, serial number, model number, etc., from the database. Once selected, the software is able to provide exact dimensional specifications of the implant. In various embodiments, centralized computing system 45 also includes a computerized joint software/templating system that combines imaging (e.g., x-rays, CT scans, etc.) of the patient's bony anatomy with overlay schematics of the replacement prosthesis (i.e., templating) to further aid in the joint reconstruction.

Robotic arm 50 (or any form of robotic assisted joint replacement application) is in communication, wired or wireless (e.g., via wireless transmitter, infrared line-of-sight sensor(s), etc.), with centralized computing system 45. An initial baseline position and orientation of robotic arm 50 is registered with centralized computing system 45 prior to a procedure (or intra-operatively). Thereafter, centralized computing system 45 tracks all movement of robotic arm 50, e.g., using line-of-sight sensors, inertial sensors, etc. Based on changes in the position and orientation of robotic arm 50, relative to its respective baseline position and orientation, centralized computing system 45 can determine the real-time position and orientation of robotic arm 50.

Robotic arm 50 may be fully automated or semi-automated. In an embodiment, whereby robotic arm 50 is fully automated, robotic arm 50 operates independent of physical assistance/intervention from a human, based on instructions provided by the centralized computing system 45. Conversely, in an embodiment, whereby robotic arm 50 is semi-automated, robotic arm 50 is, at least in-part, physically, i.e., manually, guided by a human, subject to pre-defined boundaries set by the centralized computing system 45, to carry out a defined task. Cutting tool 55, e.g., a burr-tip rotary tool, an ultrasonic reciprocating blade, chisel, flexible pin, blade, water jet, etc., is attached to robotic arm 50. The real-time position and orientation of femoral stem 5 is constantly determined by positioning system 15 and tracked by centralized computing system 45. This information, along with the dimensional aspects of femoral stem 5, as provided by the CAD software program, is processed by centralized computing system 45. Centralized computing system 45 then communicates instructions for cutting around femoral stem 5, based on a set of parameters output by the CAD software program and a real-time position and orientation of femoral stem 5, as localized by positioning system 15. By providing these calculated instructions in real-time, robotic arm 50 is able to carve femoral stem 5 from the patient's femur with maximized precision and accuracy (similar to that of a CNC router), increased efficiency and minimal bone loss, thus mitigating undue stress and potential for surgical complications to the patient. Further, because the instructions to robotic arm 50 are based, at least in-part, on real-time positional data of the implant, robotic arm 50 is able to respond to movements of femoral stem 5 in real-time without losing accuracy and precision.

Figure 2:
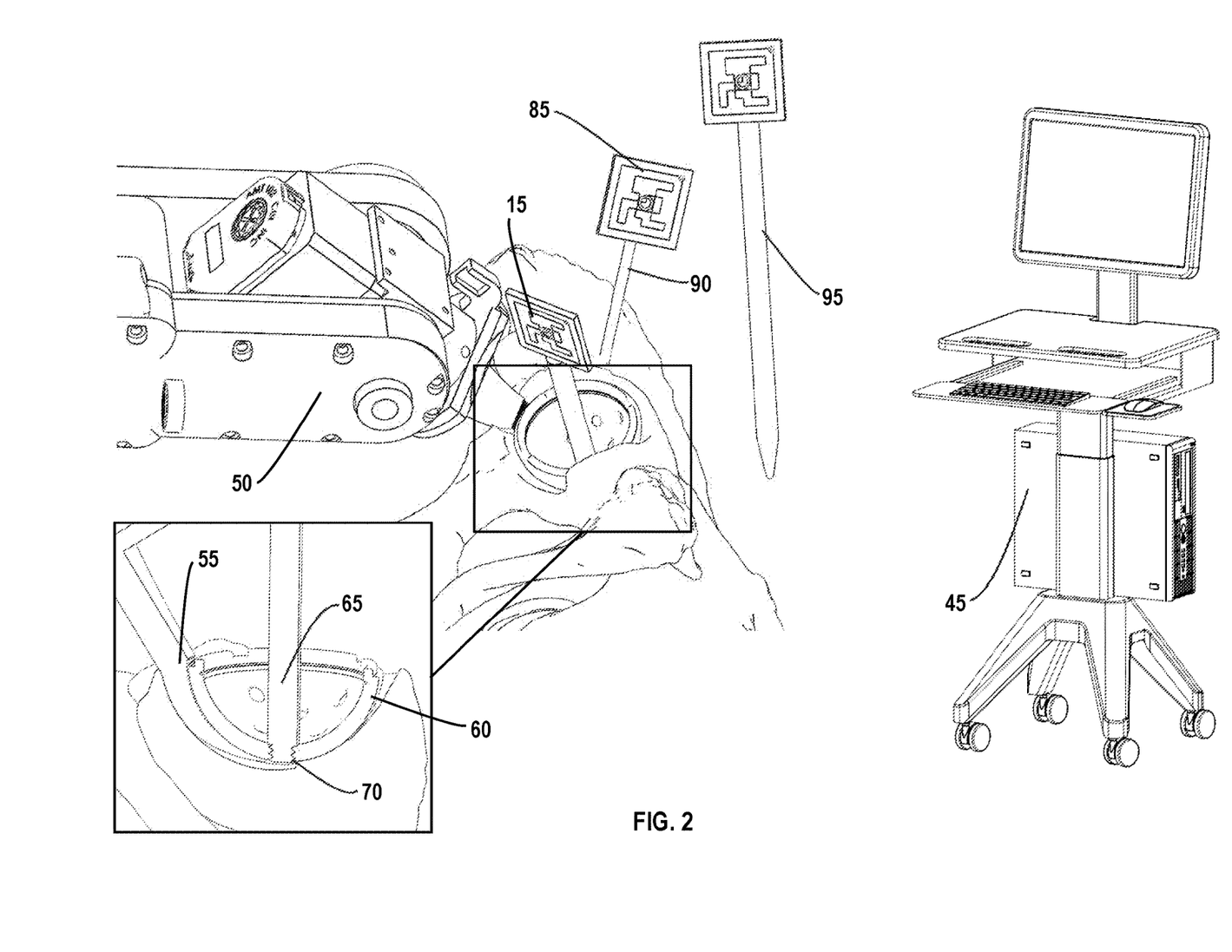
FIG. 2 shows the joint implant extraction and placement system in use with an acetabular cup, according to an embodiment of the present invention.

With reference to FIG. 2, the joint implant extraction system is shown in use with hip cup 60. Coupler 65 is rod-shaped, whereby at least one end of coupler 65 is threaded and is configured to releasably engage central aperture/orifice 70 of hip cup 60 by threaded engagement. The opposite end of coupler 65 may also be threaded, or otherwise configured, to releasably engage an object, such as handle or extraction tool (e.g., a slap-back member, pneumatic extraction device, mallet impaction plate, robotic arm etc.) to assist with extraction of hip cup 60. Just as described above in relation to coupler 10, positioning system 15 is connected to or, alternatively, integrated within, coupler 65. Once engaged, coupler 65 is secured into position in hip cup 60, whereby hip cup 60, coupler 65, and positioning system 15 are fixed, i.e., immobilized, relative to one another, such that the position and orientation of hip cup 60 is determinable, real-time, by centralized computing system 45, based on the real-time data received by centralized computing system 45 from positioning system 15.

In embodiments in which robotic arm 50 is guided by navigation only (e.g. line-of-sight array, etc.), in response to instructions from centralized computing system 45, as determined based on implant data received from the CAD software program and positioning system 15, robotic arm 50 moves independently of coupler 65 to facilitate excision of hip cup 60 using cutting tool 55. Alternatively, robotic arm 50 can attach directly to coupler 65 (rod shaped) and move along the length of coupler 65 to localize hip cup 60, whereby positioning system 15 may not be required.

In an embodiment, as shown in FIG. 2, the inner radius of curvature of cutting tool 55, i.e., that which corresponds to the edge of cutting tool 55 that is in physical communication with hip cup 60 during the excision/extraction procedure, is complementary to the exterior radius of curvature of hip cup 60. If CAD data is not available or cup size is unknown, probe 95 can be used to "paint" the surfaces of hip cup 60 to provide real-time implant dimension data to the centralized computing system 45. Probe 95 includes a positioning system (e.g., line-of-sight sensor) configured to communicate with centralized computing system 45. As the user "paints" the surface of the implant, data points are communicated to centralized computing system 45. The CAD program then uses the data to extrapolate contour and dimensional data for the implant. Depending on the software, painting may include, for example, shading/painting a defined portion of the hip cup 60, the entire surface of hip cup 60, or outlining the surfaces of hip cup 60.

Figure 3:
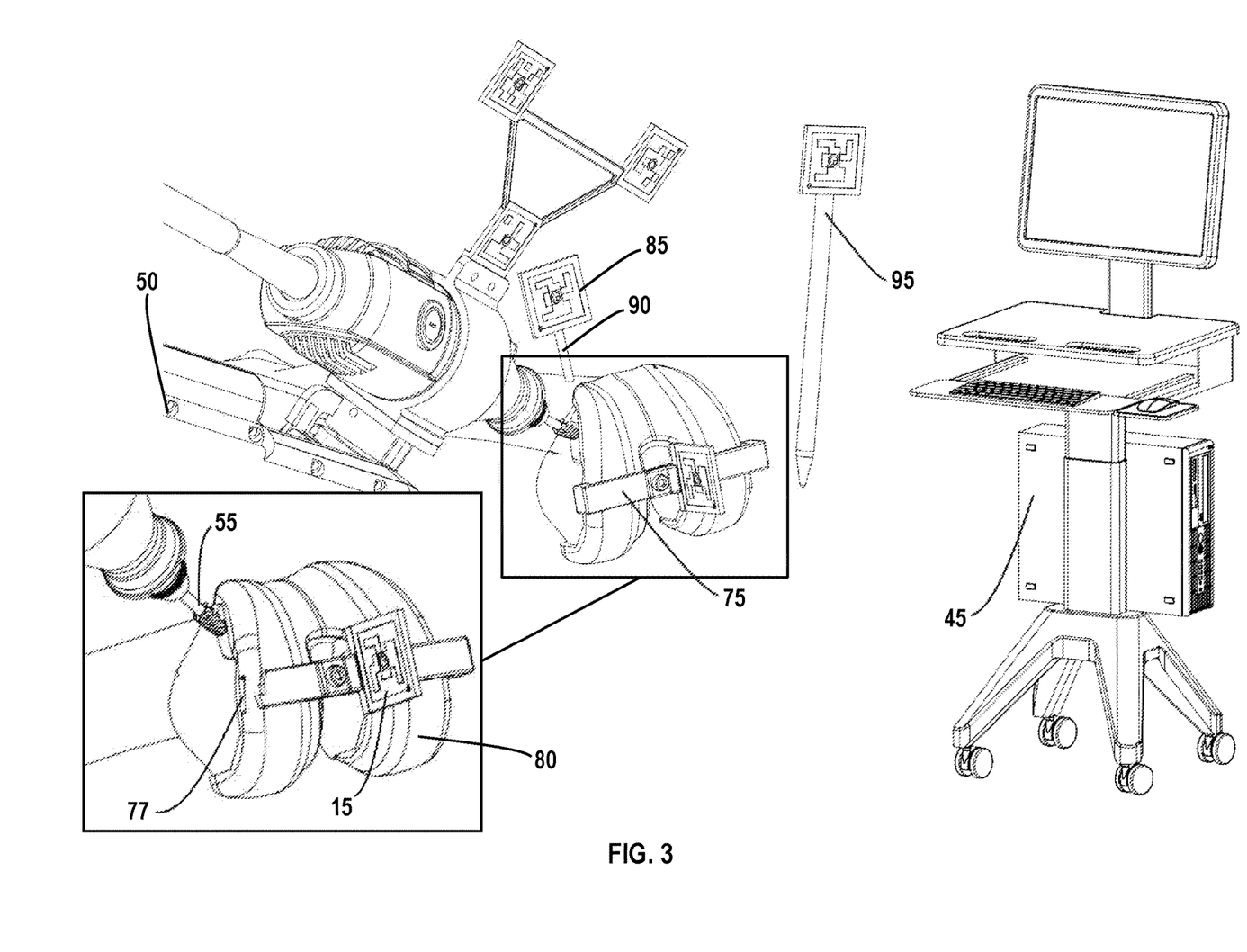
FIG. 3 shows the joint implant extraction and placement system in use with a total knee femoral component, according to an embodiment of the present invention.

With reference to FIG. 3, the joint implant extraction system is shown in use with total knee femoral component 80. Coupler 75 is shaped like a vice grip, whereby coupler 75 clamps each side of the implant and releasably engages femoral component insertion slot 77 of total knee femoral component 80 by pressure clamp engagement. The opposite end of coupler 75 may also be threaded, or otherwise configured, to releasably engage an object, such as handle or extraction tool (e.g., a slap-back member, pneumatic extraction device, mallet impaction plate, robotic arm etc.) to assist with extraction of total knee femoral component 80. Just as described above, in FIG. 1., relation to coupler 10, positioning system 15 is connected to or, alternatively, integrated within, coupler 75. Once engaged, coupler 75 is secured into position in total knee femoral component 80 at notch 77, whereby total knee femoral component 80, coupler 75, and positioning system 15 are fixed, i.e., immobilized, relative to one another, such that the position and orientation of total knee femoral component 80 is determinable, real-time, by centralized computing system 45, based on the real-time data received by centralized computing system 45 from positioning system 15. In response to instructions from centralized computing system 45, as determined based on implant data received from the CAD software program and positioning system 15, robotic arm 50 moves independently of coupler 75 in embodiments in which robotic arm 50 is used to facilitate excision of total knee femoral component 80 using cutting tool 55. If CAD data is not available, probe 95 can be used to "paint" the surfaces of the total knee femoral component 80 to provide real-time implant dimension data to the centralized computing system 45 to synthesize and extrapolate the complete femoral component 80 dimensions.

Figure 4:
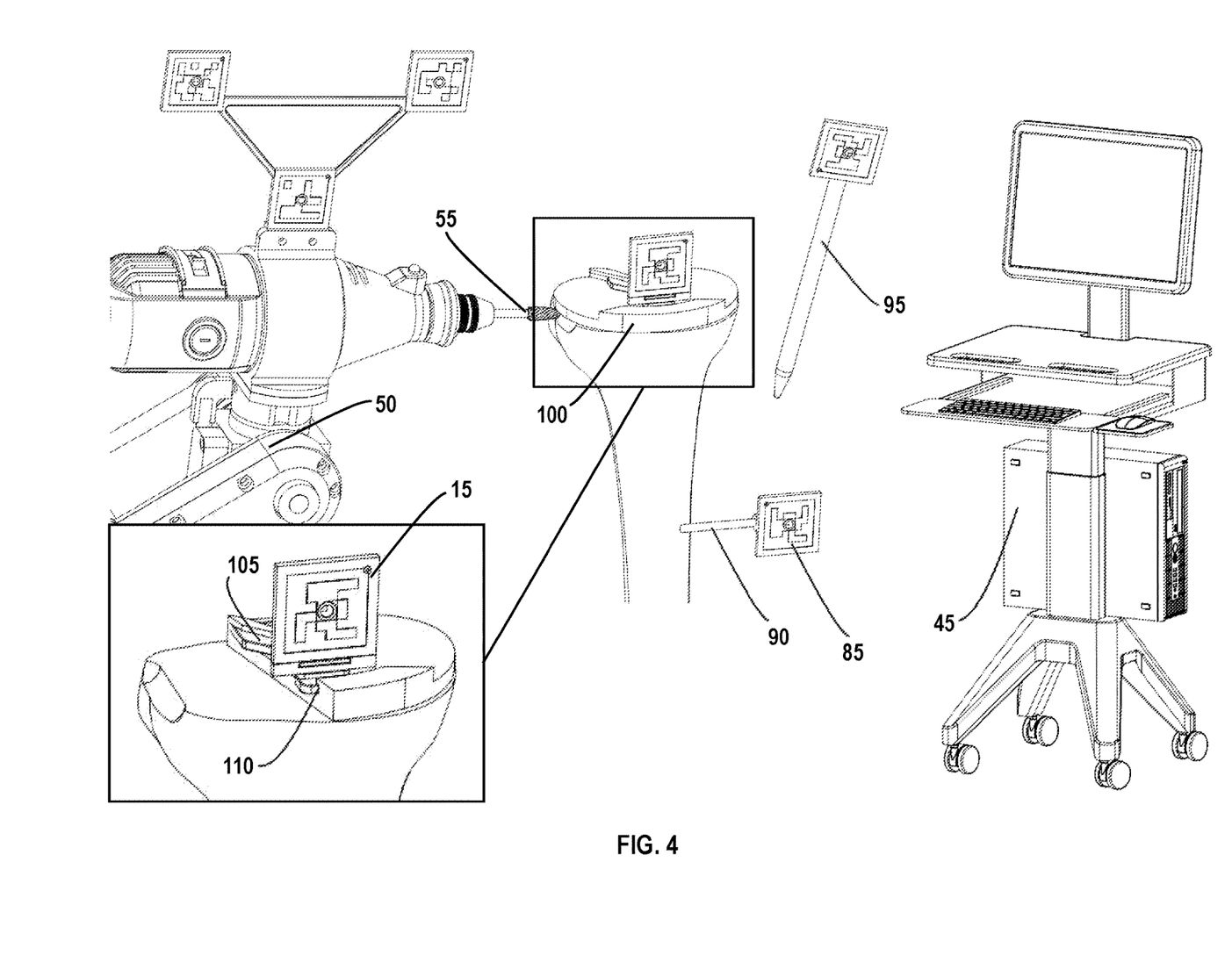
FIG. 4 shows the joint implant extraction and placement system in use with a total knee tibial component, according to an embodiment of the present invention.

With reference to FIG. 4, the joint implant extraction system is shown in use with total knee tibial component 100. Coupler 105 is shaped like a vice grip or matches tibial component locking mechanism 110, whereby coupler 105 clamps to total knee tibial component 100 locking mechanism (or sides of implant) 110 and releasably engages tibial component locking mechanism (or sides of component) 110 of total knee tibial component 100 by pressure clamp engagement. The opposite end of coupler 105 may also be threaded, or otherwise configured, to releasably engage an object, such as handle or extraction tool (e.g., a slap-back member, pneumatic extraction device, mallet impaction plate, robotic arm etc.) to assist with extraction of total knee tibial component 100. Just as described above, in FIG. 1., relation to coupler 10, positioning system 15 is connected to or, alternatively, integrated within, coupler 105. Once engaged, coupler 105 is secured into position in total knee tibial component 100, whereby total knee tibial component 100, coupler 105, and positioning system 15 are fixed, i.e., immobilized, relative to one another, such that the position and orientation of total knee tibial component 100 is determinable, real-time, by centralized computing system 45, based on the real-time data received by centralized computing system 45 from positioning system 15. In response to instructions from centralized computing system 45, as determined based on implant data received from the CAD software program and positioning system 15, robotic arm 50 moves independently of coupler 105 in embodiments in which robotic arm 50 is used to facilitate excision of total knee tibial component 100 using cutting tool 55. If CAD data is not available, probe 95 can be used to "paint" the surfaces of the total knee tibial component 100 to provide real-time implant dimension data to the centralized computing system 45 to synthesize and extrapolate the complete tibial component 100 dimensions.

Figure 5:
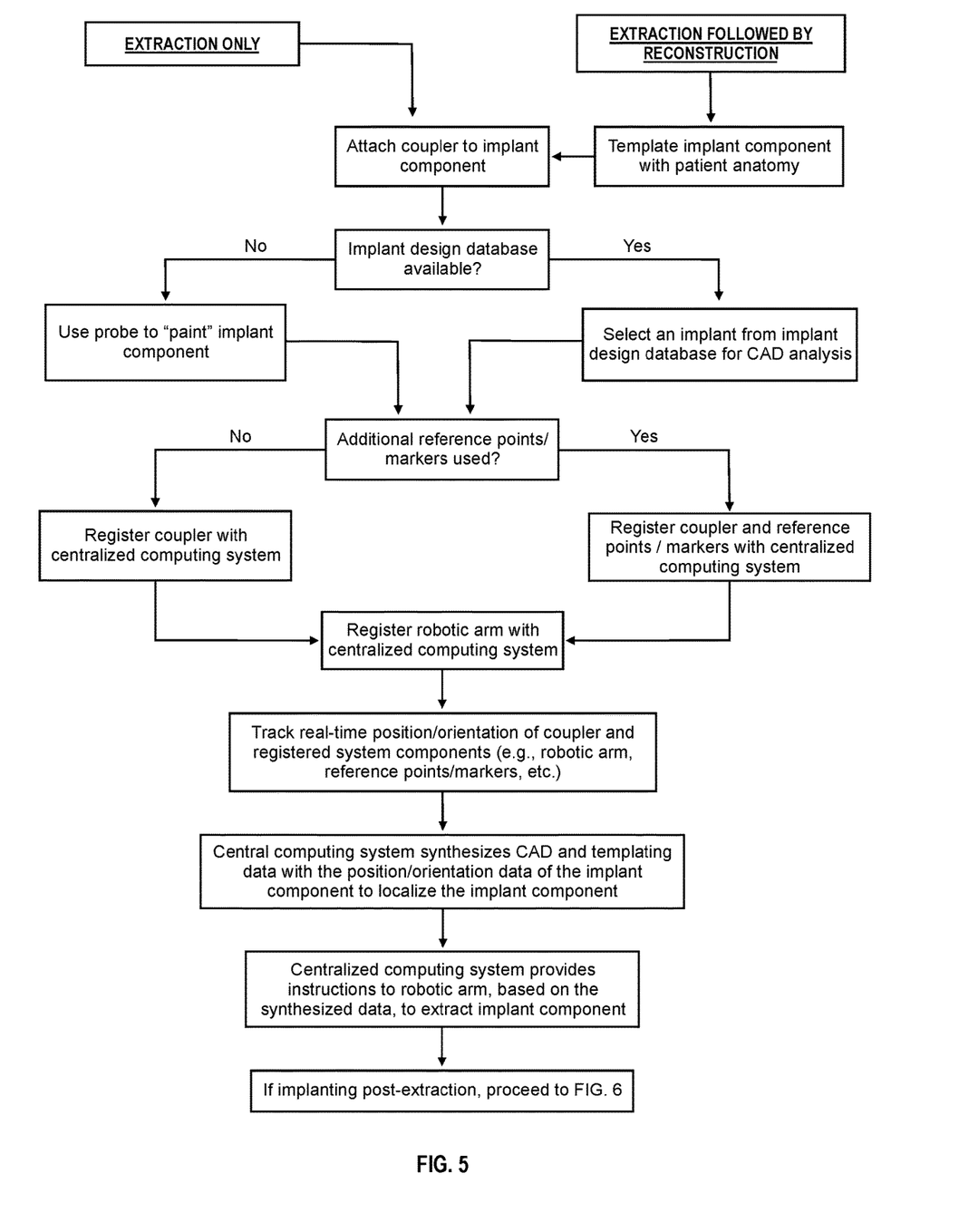
FIG. 5 is a flow chart showing a method of joint replacement implant extraction, according to an embodiment of the present invention.

The flow chart depicted in FIG. 5 summarizes the method of joint replacement implant extraction using the present system. The method outlined in FIG. 5 can be applied to any joint implant component and is provided for illustrative purposes, according to an embodiment of the present invention. Therefore, it should not be interpreted as being limiting to any particular application.

Joint Replacement Implant Placement Following Extraction

In addition to the extraction of implants in revision surgeries, the present invention can also be used to determine proper placement of an implant in real-time following implant extraction.

In an embodiment, referencing FIG. 1, the position data of original femoral stem 5 that is to be removed can be collected and used for reconstruction of the joint, following extraction of femoral stem 5. This data will guide placement of the revision components to either recreate or correct the original joint mechanics. In such an embodiment, and with respect to hip revision procedures, coupler 10 would mate to trunnion 20 to establish a fixed relationship between positioning system 15 and femoral stem 5. The initial hip mechanics/parameters would be determined prior to implant extraction based on reference markers 90/coupler 10 relationship. This is performed by placing bone reference markers 90 in the bones prior to affixing coupler 10 and positioning system 15 to femoral stem 5 for use in extraction of femoral stem 5. Bone reference markers 90 are used to reference the position of original femoral stem 5 (before extraction) in relation to the bones (e.g., femur and acetabulum/pelvis) and can register the original joint parameters (e.g., hip vertical position, leg length, medial offset, center of rotation) in centralized computing system 45. Bone reference markers 90 may be localized by centralized computing system 45 virtually via probe 95 or by transmitter 85. In an embodiment, transmitter 85 (accelerometer/gyroscope, visual array for line of sight tracking, etc.) is attached to bone reference marker 90 to provide real-time positioning data of the bones to centralized computing system 45. This allows for triangulation with positioning system 15 and coupler 10 to provide real-time positioning and orientation data of femoral stem 5 in relation to the bones. Transmitter 85 uses the same positioning technology as used in positioning system 15. Transmitter 85 and reference marker 90 may be separate units. Alternatively, transmitter 85 may be integrated into reference marker 90. After the bone reference markers 90 are registered and data collected on the original femoral stem 5 and processed by centralized computing system 45, the implant extraction can occur, as described above.

Once original femoral stem 5 is removed, the new revision femoral component (not labeled) can be placed and coupler 10 and positioning system 15 can be attached to the new femoral stem (or trial stem/broach) in the same manner as for extracted femoral stem 5. The bone reference markers 90 remain in the bone and can then be used as data reference points to reconstruct the joint parameters with the revision implants. This aids in placement of the revision implant components with real-time feedback on important joint replacement parameters in comparison to original femoral stem 5 (e.g., vertical height, leg length, offset, anteversion, etc. in hip applications. This real-time feedback on important joint replacement parameters allows the surgeon to adjust the modular features of the implants needed to correct the joint parameters prior to trialing the construct. For example, in hip revision surgery the new femoral revision component (not labeled) can be placed in the bone and the coupler 10/positioning system 15 can then be attached to the component trunnion 20 (trial or final) and register the center of rotation (which would also account for offset, leg length) against reference markers 90. If, for example, the centralized computing system 45 found the revision components' new center of rotation position to result in a construct that is 3 mm short in leg length and offset from the original extracted femoral stem 5 center of rotation position, the surgeon would immediately know the specific modular head needed to move the new center of rotation to recreate the original hip mechanics prior to reducing the hip and trialing the construct. This system would work with the same accuracy and precision even if an osteotomy was utilized to extract femoral stem 5 prior to reconstruction.

Robotic arm 50 may be used to help place the revision femoral component, whereby robotic arm 50 prepares the bone using cutting tool 55 (e.g., a pneumatic broach, reamer, burr, chisel, etc.) to match the templated/desired revision femoral component (not labeled) and robotic arm 50 is then attached to the insertion point of the revision femoral component, whereby robotic arm 50 inserts femoral stem using an insertion tool 56 (e.g., a pneumatic inserter, manual impaction with robotic assist etc.) to desired position based on the spatial relationship between reference markers 90, coupler 10, and positioning system 15. Coupler 10 could be attached during robotic arm 50 insertion of new revision femoral stem (not labeled) or attached immediately after insertion to determine implant position/joint mechanics. Alternatively, the bone can be prepared manually and the implant may be placed manually by the surgeon without the use of robotic arm 50, whereby the surgeon uses navigation system 58 via positioning system 15 and coupler 10 now attached to new revision femoral component (or placed on new revision femoral component after implantation) and manually inserts the implant (or trial component/broach) prior to referencing its position as described above.

In another embodiment, in reference to FIG. 2., bone reference markers 90 may be attached to the pelvis to help guide placement of new revision hip cup (not labeled) after extraction of original hip cup 60. Additionally, bone reference markers 90 can serve as a reference point, designating hip center on the pelvis. Reference markers 90 may be anchored to the patient's bone. Alternatively, in reference to FIGS. 1-2, reference markers 90 may be a superficial registration point, e.g., an EKG lead patch placed on the skin, to serve as a reference point to judge leg length, for example.

In another embodiment, referencing FIGS. 3-4, this application can also be applied to implant placement in revision surgical procedures following extraction of the implants in total knee revision procedures. Coupler 75/105/positioning system 15 would mate, as described above to total knee femoral component 80 and/or total knee tibial component 100 to establish a fixed relationship between positioning system 15 on total knee femoral component 80 and total knee tibial component 100 (each independently or in conjunction) with bone reference markers 90. Reference markers 90 would be placed in the femur and tibia bones and registered. The initial static knee mechanics/parameters would be determined prior to implant extraction based on reference marker 90/coupler 75/105/positioning system 15 relationship. The centralized computing system 45 determines the position of the original implant component's joint line, extension/flexion gaps, etc. This may or may not include additional reference points (e.g. epicondyles, etc.) as identified virtually with probe 95 to increase accuracy prior to extractions. Alternatively, or in addition, dynamic ligamentous tension and gap balancing could be determined without couplers 75/105 attached, or prior to attaching couplers 75/105, with only reference markers 90 in place during knee range of motion/ligament/gap balance testing. This is measured by the surgeon performing a range of motion, ligament stress test, etc. with reference markers 90 affixed to the femur and tibia to record the dynamic data of the knee joint (e.g. flexion/extension gap during range of motion, hip center of rotation, ligament tension, etc.) Once static and dynamic data is calculated by centralized computing system 45, in conjunction with or without fluoroscopy templating, the original implants total knee femoral component 80 and total knee tibial component 100 are excised as described above in the implant extraction technique. In an embodiment, the extraction process could also use the data collected on original total knee femoral component 80 and original total knee tibial component 100 to guide bone preparation for the new revision components (not labeled) as part of the extraction process. As an example, in current techniques the femoral bone must be cut/prepared to fit the new revision total knee femoral component following extraction of original total knee femoral component 80. In the present invention, centralized computing system 45 (knowing static and dynamic data regarding original total knee joint mechanics and position of total knee femoral component 80/total knee tibial component 100 against reference markers 90) could guide robotic arm 50 and cutting tool 55 to prepare the bone to accept the new revision total knee components as part of extraction. For example, if an additional distal femoral 4 mm augment on the new total knee revision femoral component would be planned to recreate the joint line, robotic arm 50 and cutting tool 55 could cut an additional 4 mm of bone (behind original total knee femoral component 80) which would simultaneously allow for extraction of original total knee femoral component 80 and preparation of bone for new implant placement. The ability to simultaneously extract the implant and prepare the bone for reconstruction with new revision implants would significantly increase the efficiency of the reconstruction process as well as increase accuracy and precision. As one can imagine, this application for simultaneous reconstruction would work for both the new revision femur and tibial components (not labeled) and augments in all positions (e.g., posterior femoral condyles, tibial augments, distal femoral augments, etc.) as well as specific component parameters (e.g., rotation, flexion of femoral component, tibial component slope, etc.) Once the implants are extracted, robotic arm 50 could also be used (based on the above data) to prepare the canal for a broach and/or stem attachment(s) to new revision components (e.g., reamers, pneumatic broach inserter, etc.) as depth of insertion for a broach or stem could be determined based on original joint line data collected prior to extraction of original total knee femoral component 80 and total knee tibial component 100. The reference markers 90 are kept in the bone throughout the process of extraction and reconstruction, as are any additional reference points identified by probe 95, and are used by the surgeon to obtain real-time feedback at the time of reconstruction on the knee parameters (e.g., joint line reconstruction, gap balance, augment thickness/location required, polyethylene thickness, etc.). This allows for accurate positioning of the new revision femoral component (not labeled)/new tibial revision component (not labeled), which can be trial or final components, in relation to the original implant component position/joint parameter data collected. The accuracy of the joint reconstruction with the revision components can then be assessed by reattaching couplers 75/105 and positioning system 15, respectively, to the new revision components to reference against the bone reference markers 90 upon insertion (to check static parameters) and prior to trialing the new revision components (dynamic parameters). If extraction occurred without specific robotic arm 50 bone preparation to match planned new revision components and bone is prepared via traditional methods (e.g., cutting blocks affixed, intramedullary rods, etc.), additional reference points as defined by probe 95 after extraction may be required (e.g., to re-register ("paint") the location of the remaining femoral bone/tibia against the reference markers 90 placed before extraction of the implant). This would facilitate more efficient selection of augments for cutting blocks for bone preparation and for the correct femoral modular component selection (e.g., femoral size, augments, etc.) and tibial modular component selection (e.g., tibial augments, polyethylene insert thickness) needed to recreate or correct the original total knee mechanics prior to extraction. The knee can then be more efficiently trialed. During trialing coupler 75/105 may be removed and dynamic joint data (ligament tension, gap balancing, etc.) can be obtained with reference markers only 90 as performed prior to extraction.

Figure 6:
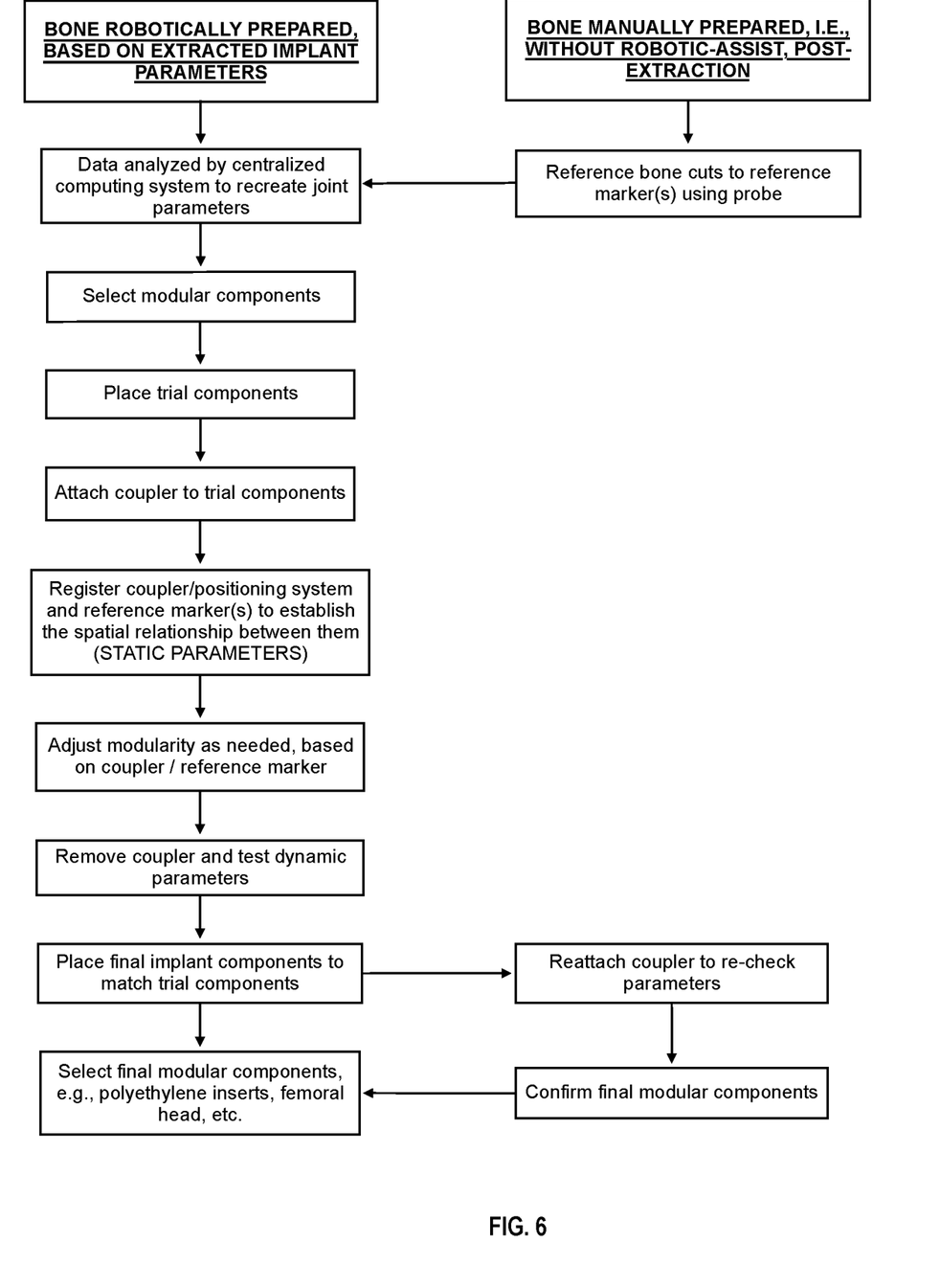
FIG. 6 is a flow chart showing a method of joint replacement implant placement following extraction, according to an embodiment of the present invention.

The flow chart depicted in FIG. 6 summarizes the method of joint replacement implant placement following implant extraction using the present system. The method outlined in FIG. 6 can be applied to any joint implant component and is provided for illustrative purposes, according to an embodiment of the present invention. Therefore, it should not be interpreted as being limiting to any particular application.

Primary Hip Replacement Femoral Component Insertion

In an embodiment, with reference to FIG. 1, the present invention can also be applied to implant placement in primary hip replacement surgical procedures.

In this embodiment, no extraction is needed so cutting tool 55 will not be used to excise a component. However, cutting tool 55 may be used to prepare the bone for implant placement as described below. In this embodiment, an x-ray/fluoroscopic image of the joint is taken intraoperatively for real-time templating purposes. When utilizing an intraoperative film or fluoroscopy, one or more reference markers 90 are attached to the patient in the area to be imaged prior to taking the image. In one embodiment, the reference markers 90 are attached to the proximal femur as a cortical button and are calibrated (known dimensions) to aid in scaling for templating by centralized computing system 45 and allow for determining the native hip center of rotation position in relation to reference markers 90. In another embodiment, reference marker 90 may be a superficial registration point, e.g., an EKG lead patch placed on the skin, to serve as a reference point to judge leg length, for example. Superficial registration points are often, but not always, used in conjunction with advanced imaging, e.g., a CT, MRI, or EOS scan. Based on information transmitted from the radiographic image/template/reference marker 90 scaling and position of the native hip center of rotation, centralized computing system 45 can calculate/template the joint, e.g., the hip, and also can use the opposite joint, i.e., the opposite hip, as a reference to compare differences between the two joints. With this information, reference marker 90 can then be checked at the time of insertion of femoral component 5. This is done, for example, by placing probe 95 on the cortical button, i.e. reference marker 90, whereby computing system 45 determines the position of femoral stem 5 center of rotation, as defined by coupler 10 and positioning system 15 attached to femoral stem 5 trunnion 20 as described above, as referenced against the reference marker 90. Alternatively, if the transmitter 85 is built into the reference marker 90, probe 95 may not be required since the reference point would register immediately in real time. Thus, the surgeon can determine, real-time what adjustments are made and, hence, what exact further adjustments need to be made to recreate the native hip mechanics, center of rotation, offset, and leg lengths. For example, the surgeon would know immediately whether a particular adjustment changed the center of rotation and lengthened, shortened, increased offset, decreased offset, or altered version of the joint's associated anatomy. Additionally, centralized computing system 45 can instruct the surgeon on what implant (e.g., modular head adjustment, adjust implant placement, etc.) to use to accomplish the appropriate corrective measures. For example, centralized computing system 45 can determine what modular femoral head/neck length is needed to restore the appropriate leg length/anatomy/offset, etc., based on the initial x-ray/template and utilizing the spatial relationship (i.e., triangulation) between reference markers 90, coupler 10, and positioning system 15. Coupler 10 and positioning system 15 construct may also connect to a broach or trial implant (not shown) to provide the same real-time information on seating of the broach or trial implant prior to placement of final implant femoral stem 5.

By providing real-time analysis, positional and orientation data of the implant, etc., during the seating process of the implant, or immediately after seating, e.g., femoral stem 5, the surgeon is able to determine, without interruption and with absolute precision and accuracy, what adjustments must be made for proper seating of the implant. The system instructs the surgeon with real-time feedback on leg length, stem seating height within the femur, and position of femoral stem 5 in relation to the pre-op plan/component position/reference markers 90 desired by the surgeon. This facilitates more efficient selection of the correct size broach/trial stem, final femoral stem as well as the modular femoral head required to correct leg length and offset based on the position of femoral stem 5. The real-time information of femoral stem 5 provides the exact vertical height, offset and the femoral anteversion of femoral stem 5 so the surgeon can make adjustments, as needed, based on intraoperative findings and with comparison to the template to restore the desired hip mechanics/parameters, thereby significantly reducing the risk of placing femoral stem 5 in varus or under-sizing the component and mitigating the risk of intra-operative fracture as well as decreasing the risk of dislocation. In addition to ensuring proper placement of the implant, the need for intermittent scans is obviated, reducing overall procedure time and x-ray/fluoroscopic exposure to the patient and surgical team.

Utilizing this system for the placement of primary femoral stem 5 may employ robotic arm 50 to help place femoral stem 5, whereby robotic arm 50 prepares the bone using cutting tool 55 (e.g., a pneumatic broach, reamer, burr, chisel, etc.) to match templated/desired revision femoral component (not labeled) and robotic arm 50 is then attached to the insertion point of femoral stem 5, whereby, robotic arm 50 inserts femoral stem 5 (e.g., using pneumatic inserter, etc.) to desired position based on the spatial relationship between reference markers 90, coupler 10, and positioning system 15. Coupler 10 could be attached during robotic arm 50 insertion of femoral stem 5 or attached immediately after insertion to determine implant position/joint mechanics. Alternatively, the bone can be prepared manually, without robotic assistance, and the implant may be placed manually by the surgeon without the use of robotic arm 50, whereby the surgeon uses positioning system 15 and coupler 10 now attached to new femoral stem 5 and manually inserts femoral stem 5. Referencing its position against reference markers 90 as described above. Alternatively, coupler 10 and positioning system 15 can be attached after femoral stem 5 has been inserted.

Figure 7:
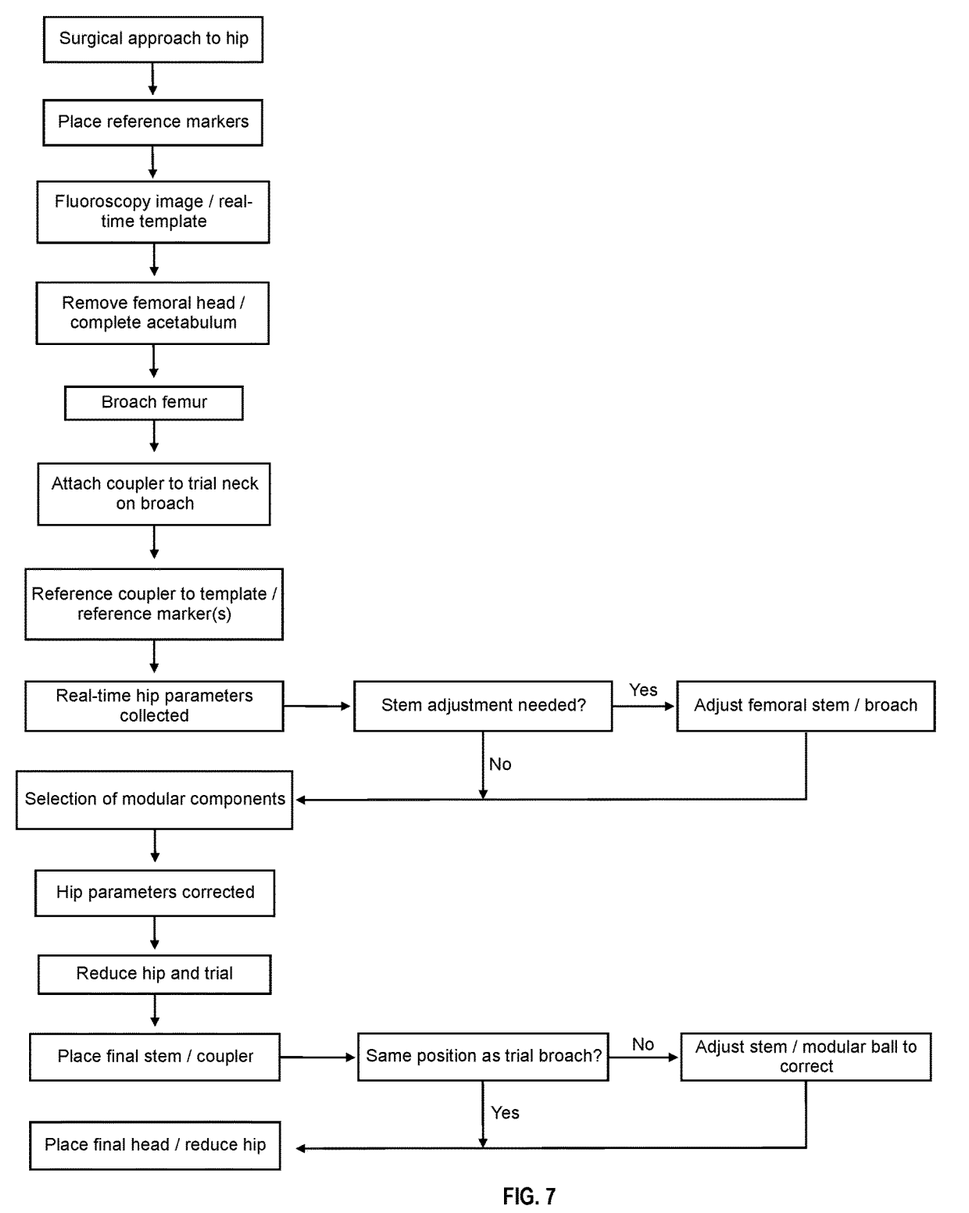
FIG. 7 is a flow chart showing a method of primary hip replacement femoral component insertion, according to an embodiment of the present invention.

The flow chart depicted in FIG. 7 summarizes the method of implant placement in primary hip replacement surgical procedures using the present system. The method outlined in FIG. 7 is provided for illustrative purposes, according to an embodiment of the present invention. Therefore, it should not be interpreted as being limiting to any particular application.

The foregoing descriptions regarding various joint revision or primary implant procedures is provided for illustrative purposes only, and is not meant to limit the scope of the invention to any particular application. One skilled in the art would understand and appreciate that the invention could be similarly applied to other joint revision or primary implant procedures other than those specifically described (i.e., the present invention can be used with any joint that is a candidate for primary replacement or revision surgery in any application described herein) without deviating from the scope of the present invention. As long as there is an anchor, e.g., a trunnion, a threaded aperture/orifice, etc., that is fixed in space, relative to the prosthetic component to be seated or removed, and can serve as a connection point to, likewise, fix the positioning system in space, in a known relationship, relative to the prosthetic component to be seated or removed, the present invention can be used to identify the exact real-time position and orientation of a prosthesis in any joint replacement, i.e., primary or revision, surgery.

The invention has been described herein using specific embodiments for the purposes of illustration only. It will be readily apparent to one of ordinary skill in the art, however, that the principles of the invention can be embodied in other ways. Likewise, it will be readily apparent that the features, functions, and/or elements of the present invention disclosed herein can be used in any combination to produce various embodiments of the present invention. Therefore, the invention should not be regarded as being limited in scope to the specific embodiments disclosed herein, but instead as being fully commensurate in scope with the following claims.

I claim:

1. A system for extracting joint implants from a bone comprising:
   a centralized computing system comprising:
      a CAD software program;
      a computer readable medium storing instructions;
      a processor; and
      a database comprising an implant design data;
   a hip femoral implant component comprising a bone engaging surface, a neck, and a trunnion,
   wherein the implant design data includes data of the implant component;
   a robotic arm in communication with the centralized computing system, the robotic arm comprising an implant extraction cutting tool; and
   an implant localization device in communication with the centralized computing system, the implant localization device comprising:
      a coupler configured to couple to the implant component via friction engagement, the coupler comprising a sleeve configured to receive the trunnion, wherein, when the trunnion is received into the sleeve, the sleeve and trunnion frictionally engage one another to fix the coupler in a known, pre-determined position and orientation relative to the implant component; and
      a positioning system comprising one or more sensors in communication with the centralized computing system, wherein the coupler and the positioning system are in a fixed position and orientation relative to one another, such that engagement of the coupler with the implant component fixes the positioning system in space, in a known, pre-determined position and orientation relative to the implant component,
   wherein the localization device is not connected to the robotic arm,
   wherein when the instructions are executed by the processor, the centralized computing system:
      determines a real-time position and orientation of the positioning system based on data from the positioning system;
      calculates a real-time position and orientation of the implant component, based on the real-time position and orientation of the positioning system without registering the bone or using additional reference points on the bone, wherein the fixed spatial relationship between the positioning system and the implant component, combined with the real-time position and orientation of the positioning system, eliminates the need for registration of the bone and use of additional reference points on the bone to calculate the real-time position and orientation of the implant component;

analyzes the implant design data via the CAD software program to render accurate dimensional data of the implant component; and provides real-time instructions to the robotic arm to extract the implant component from the bone, said real-time instructions being based on the dimensional data and real-time position and orientation of the implant component, and wherein the localization device remains coupled to the implant component while the implant extraction cutting tool is used by the robotic arm to extract the implant component from the bone.

2. The system of claim 1, wherein a starting position and orientation of the positioning system is registered with the centralized computing system, wherein the centralized computing system is configured to use real-time data from the positioning system to determine changes in position and orientation of the positioning system relative to the starting position and orientation of the positioning system, thereby allowing the computing system to calculate a real-time position and orientation of the positioning system.

3. The system of claim 1, wherein, when the instructions are executed by the processor, the centralized computing system determines a real-time position and orientation of the robotic arm relative to the real-time position and orientation of the implant component, wherein the robotic arm is configured to execute instructions received from the centralized computing system, and wherein the real-time instructions are further based on a real-time spatial relationship between the robotic arm and the implant component.

4. The system of claim 1, wherein the positioning system is integrally formed as part of the coupler.

5. The system of claim 1, wherein the positioning system is removably coupled to the coupler.

6. The system of claim 1, wherein the one or more sensors comprises at least one of an accelerometer and a gyroscope.

7. The system of claim 1, wherein the one or more sensors comprises a sensor array.

8. The system of claim 1, further comprising a probe in communication with the centralized computing system, wherein the probe is configured to register virtual reference points on the implant component when data of the implant component is not available in the database, wherein the CAD software program is further configured to extrapolate contour and dimension data of the implant component, based on the virtual reference points.

9. A system for reconstructing a hip femoral implant component comprising the system of claim 1, and further comprising one or more reference markers, wherein the one or more reference markers are registered with the centralized computing system, wherein the centralized computing system is configured to determine a real-time position and orientation of the one or more reference markers relative to the real-time position and orientation of the implant component and the robotic arm, wherein the real-time instructions are further based on the real-time position and orientation of the one or more reference markers relative to the real-time position and orientation of the implant component and the robotic arm.

10. The system of claim 9, further comprising a probe configured to register the one or more reference markers with the centralized computing system, wherein the centralized computing system is configured to analyze a real-time position and orientation of the coupler relative to the real-time position and orientation of the one or more reference markers to determine real-time joint parameters of the implant component.

11. The system of claim 9, further comprising:
a joint templating software program configured to compare joint scans with overlay schematics of the implant component,
wherein the real-time instructions are further based on data from the joint templating software program.

* * * * *